United States Patent
Holstein et al.

(10) Patent No.: US 8,735,005 B2
(45) Date of Patent: May 27, 2014

(54) FLUORINATED CYCLIC CARBONATES AND COMPOSITIONS THEREOF

(75) Inventors: William L. Holstein, Hockessin, DE (US); Xudong Chen, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 607 days.

(21) Appl. No.: 13/078,655

(22) Filed: Apr. 1, 2011

(65) Prior Publication Data

US 2011/0244313 A1  Oct. 6, 2011

Related U.S. Application Data

(60) Provisional application No. 61/320,370, filed on Apr. 2, 2010, provisional application No. 61/320,373, filed on Apr. 2, 2010.

(51) Int. Cl.
*H01M 10/0569* (2010.01)
*C07D 317/34* (2006.01)

(52) U.S. Cl.
USPC ............ 429/338; 429/331; 429/332; 549/229

(58) Field of Classification Search
USPC ........................... 429/331, 332, 338; 549/229
See application file for complete search history.

(56) References Cited

U.S. PATENT DOCUMENTS

| | | |
|---|---|---|
| 5,659,062 A | 8/1997 | Yokoyama et al. |
| 5,847,156 A | 12/1998 | Eldin et al. |
| 6,534,220 B2 | 3/2003 | Garbe |
| 2007/0148540 A1 | 6/2007 | Chiga et al. |

FOREIGN PATENT DOCUMENTS

WO  2008/079670 A1  7/2008

*Primary Examiner* — Carlos Barcena
*Assistant Examiner* — Lilia V Nedialkova

(57) ABSTRACT

Novel fluorinated cyclic carbonate compounds are described. These compounds may be useful as non-aqueous electrolyte solvents, specialty solvents, and starting materials and intermediates for synthesis of dyes, agricultural chemicals, and pharmaceuticals.

18 Claims, No Drawings

FLUORINATED CYCLIC CARBONATES AND COMPOSITIONS THEREOF

This application claims priority under 35 U.S.C. §119(e) from, and claims the benefit of, U.S. Provisional Application No. 61/320,370 (filed Apr. 2, 2010) and U.S. Provisional Application No. 61/320,373 (filed Apr. 2, 2010), each of which is by this reference incorporated in its entirety as a part hereof for all purposes.

TECHNICAL FIELD

The invention relates to novel fluorinated cyclic carbonate compounds, which are useful as nonaqueous solvents having excellent anti-oxidation properties.

BACKGROUND

Carbonate compounds are useful as specialty solvents in fields such as pharmaceutical and agricultural chemistry, and as starting materials and intermediates in preparation of dyes, agricultural chemicals, and pharmaceuticals. Carbonate compounds are also used as electrolyte solvents for non-aqueous batteries containing cathodes made from alkali metals, alkaline earth metals, or compounds comprising these metals, for example lithium ion batteries.

Current lithium ion battery electrolyte solvents typically contain one or more linear carbonates, such as ethyl methyl carbonate, dimethyl carbonate or diethylcarbonate; and a cyclic carbonate, such as ethylene carbonate. However, at battery voltages above 4.4V, these electrolyte solvents can decompose and cause a loss of battery performance. Additionally, there are safety concerns with the use of these electrolyte solvents because of their low boiling point and high flammability.

To overcome the limitations of conventional nonaqueous electrolyte solvents, several new carbonate compounds have been developed. For example, U.S. Pat. No. 5,659,062 describes carbonate compounds given by the general formula $R^1CH_2O$—CO—$OCH_2R^2$, wherein $R^1$ represents a hydrogen atom, an alkyl group, or an alkyl group substituted with one or more halogen atoms, and $R^2$ represents an alkyl group having no hydrogen atom at the •-position thereof or an alkyl group substituted with one or more halogen atoms and having no hydrogen atom at the •-position thereof, with the proviso that $R^1$ is not identical to $R^2$. Additionally, WO 08/79670 describes fluorinated cyclic and acyclic carbonate solvents such as various fluorine-substituted 1,3-dioxolane-2-one compounds and fluorine-substituted 1,3-dioxane-2-one compounds.

A need still remains, however, for electrolyte solvents that are highly stable to oxidation and have a high boiling point.

SUMMARY

This invention addresses the above need by providing novel fluorinated cyclic carbonate compounds as described herein.

Accordingly, in one embodiment, the inventions hereof provide a compound represented by the following structure:

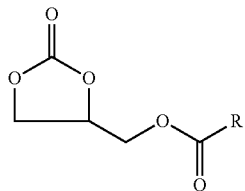

wherein R is a $C_1$ to $C_4$ fluoroalkyl group.

In another embodiment, the inventions hereof provide a process for preparing a compound as described above by combining, optionally in a solvent, glycerol 1,2-carbonate and $(RfCO)_2O$ or RfCOX, wherein Rf is $C_1$ to $C_4$ fluoroalkyl and X is halogen.

In a further embodiment, the inventions hereof provide a composition that includes a compound as described above and at least one electrolyte salt.

In yet another embodiment, the inventions hereof provide an electrochemical cell that includes (a) a housing; (b) an anode and a cathode disposed within the housing; (c) a porous separator disposed within the housing between the anode and the cathode; and (d) an electrolyte composition disposed within housing in contact with the anode, the cathode and the porous separator and providing an ionically-conductive pathway between said the anode and the cathode, wherein the electrolyte composition includes at least one electrolyte salt and a compound as described above.

In yet another embodiment, the inventions hereof provide an article that includes an electrochemical cell as described above.

The inventions hereof thus provide novel fluorinated cyclic carbonate compounds that can be used as non-aqueous electrolyte solvents, as well as specialty solvents, and as starting materials and intermediates for synthesis of dyes, agricultural chemicals, and pharmaceuticals. As electrolyte solvents, these compounds are highly stable to oxidation and have a high boiling point, and thus can be used in non-aqueous battery systems, such as lithium ion batteries.

DETAILED DESCRIPTION

As used above and throughout the description of the inventions hereof, the following terms, unless otherwise indicated, shall be defined as follows:

The term "alkyl group" refers to a straight or branched chain hydrocarbon group containing no unsaturation.

The term "anode" refers to the electrode of an electrochemical cell, at which oxidation occurs. In a galvanic cell, such as a battery, the anode is the negatively charged electrode.

The term "cathode" refers to the electrode of an electrochemical cell, at which reduction occurs. In a galvanic cell, such as a battery, the cathode is the positively charged electrode.

The term "electrolyte composition" refers to a chemical composition suitable for use as an electrolyte in an electrochemical cell. An electrolyte composition typically includes at least one solvent and at least one electrolyte salt.

The term "electrolyte salt" refers to an ionic salt that is at least partially soluble in the solvent of an electrolyte composition and that at least partially dissociates into ions in the solvent of the electrolyte composition to form a conductive electrolyte composition.

The term "fluoroalkyl" refers to an alkyl group wherein one or more fluorines have been substituted for one or more hydrogens.

The term "lithium ion battery" refers to a type of rechargeable battery in which lithium ions move from the anode to the cathode during discharge, and from the cathode to the anode during charge.

In one embodiment of the inventions hereof, there are disclosed novel fluorinated cyclic carbonate compounds. These compounds can, in various embodiments, be used as electrolyte solvents for non-aqueous battery systems, such as lithium ion batteries, and can also be used as specialty solvents and starting materials and intermediates for organic synthesis.

The fluorinated cyclic carbonate compounds disclosed herein are represented by the following structure:

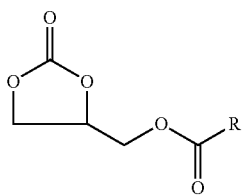

(1)

wherein R is a $C_1$ to $C_4$ fluoroalkyl group.

In one embodiment, for example, in a $C_n$ fluoroalky group (where n=1~4), there can be any number of fluorine atoms between 1 and 2n+1 located on any of the carbon atoms. In another embodiment, for example, the cyclic carbonate compound is 2-oxo-1,3-dioxolan-4-yl)methyl 2,2,2-trifluoroacetate, wherein R in the structure of Formula (1) is $CF_3$. In another embodiment, the cyclic carbonate compound is 2-oxo-1,3-dioxolan-4-yl)methyl 2,2-difluoroacetate, wherein R in the structure of Formula (1) is $CF_2H$.

These fluorinated cyclic carbonate compounds can be prepared by a process that includes combining glycerol 1,2-carbonate and $(RfCO)_2O$ or RfCOX, wherein Rf is C1 to C4 fluoroalkyl and X is a halogen such as F, Cl, Br or I. In other alternative embodiments, glycerol 1,2-carbonate can be combined with RfCOOH.

These materials are contacted when they are combined, and react to produce a carbonate compound as described herein. The process may be carried out in an optional solvent. Suitable solvents include without limitation polar aprotic solvents such as dichloromethane, chloroform, ether, and tetrahydrofuran. In one embodiment, for example, the solvent is dichloromethane. The glycerol 1,2-carbonate and $(RfCO)_2O$ or RfCOX may be combined in any suitable reaction vessel. Typically, the optional solvent is dried and the reaction is carried out in a dry box or under nitrogen protection to exclude moisture from the air.

Reaction conditions for the process may vary. For example, reaction temperatures may vary depending on a number of factors such as the concentration of reactants, the stability of the product formed, reaction time and yield desired. Suitable temperatures range from 0° C. up to refluxing conditions. In some embodiments, the reaction is carried out at room temperature (i.e. approximately 20° C.).

The resulting mixture is mixed for a time sufficient for the formation of the fluorinated cyclic carbonate product, typically 3 to 4 hours. After this time, volatile components may be removed using methods known in the art, such as evaporation under vacuum. The product may be recovered and purified using standard methods such as vacuum distillation or column chromatography.

In one embodiment, for example, $(RfCO)_2O$ is trifluoroacetic anhydride, i.e. $(CF_3CO)_2O$, the use of which is described in detail in Example 1 herein. In another embodiment, $(RfCO)_2O$ is difluoroacetic anhydride, i.e. $(CF_2HCO)_2O$, as described in detail in Example 2 herein.

The fluorinated cyclic carbonate compounds disclosed herein may be used in various applications including without limitation as non-aqueous electrolyte solvents, specialty solvents, and starting materials and intermediates for synthesis of dyes, agricultural chemicals, and pharmaceuticals. The fluorinated cyclic carbonate compounds disclosed herein may be particularly useful as electrolyte solvents for non-aqueous batteries containing cathodes made from alkali metals, alkaline earth metals, or compounds comprising these metals, for example lithium ion batteries.

In one embodiment of the inventions hereof, there is provided an electrolyte composition that includes at least one fluorinated cyclic carbonate compound as set forth in the structure of Formula (I) and at least one electrolyte salt, wherein the electrolyte salt is at least partially soluble in the fluorinated carbonate compound at the desired operating temperature. The electrolyte composition may further include one or more co-solvents, and various additives known in the art such as a surfactant. In a lithium ion battery, for example, the electrolyte composition may comprise at least one co-solvent selected from ethyl methyl carbonate, dimethyl carbonate, diethyl carbonate, ethylene carbonate, propylene carbonate, vinylethylene carbonate, fluoroethylene carbonate, 2,2,2-trifluoroethyl carbonate, and methyl 2,2,3,3-tetrafluoropropyl carbonate.

The fluorinated cyclic carbonate compound as set forth in the structure of Formula (1) and a co-solvent may be combined in various ratios depending on the desired properties of the electrolyte composition, which can be readily determined. In one embodiment, for example, the fluorinated cyclic compound can be about 5% to about 60% of the solvent mixture by weight. In another embodiment, the fluorinated cyclic compound can be about 20% to about 40% of the solvent mixture by weight. In another embodiment, the fluorinated cyclic can be about 25% to about 35% of the solvent mixture by weight.

In an alternative embodiment, the electrolyte composition can be a mixture of 2,2,2-trifluoroethyl carbonate and 2-oxo-1,3-dioxolan-4-yl)methyl 2,2,2-trifluoroacetate or 2-oxo-1,3-dioxolan-4-yl)methyl 2,2-difluoroacetate. In another embodiment, the electrolyte composition can be a mixture of methyl 2,2,3,3-tetrafluoropropyl carbonate and 2-oxo-1,3-dioxolan-4-yl)methyl 2,2,2-trifluoroacetate or 2-oxo-1,3-dioxolan-4-yl)methyl 2,2-difluoroacetate.

Suitable electrolyte salts for use in a lithium ion battery include without limitation those such as lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide, lithium bis(oxalato)borate, $Li_2B_{12}F_{12-x}H_x$ where x is equal to 0 to 8, and mixtures of lithium fluoride and anion receptors such as $B(OC_6F_5)_3$. In one embodiment, the electrolyte salt is lithium hexafluorophosphate.

In another embodiment, the invention provides an electrochemical cell comprising a housing, an anode and a cathode disposed in the housing and in ionically conductive contact with one another, an electrolyte composition, as described above, disposed in the housing and providing an ionically conductive pathway between the anode and the cathode, and a porous separator disposed in the housing and between the anode and the cathode.

The housing may be any suitable container to house the electrochemical cell components. The anode and the cathode may be comprised of any suitable conducting material depending on the type of electrochemical cell. Suitable examples of anode materials include without limitation lithium metal, lithium metal alloys, aluminum, platinum, palladium, graphite, transition metal oxides, and lithiated tin oxide. Suitable examples of cathode materials include without limitation graphite, aluminum, platinum, palladium, electroactive transition metal oxides comprising lithium, indium tin oxide, and conducting polymers such as polypyrrole and polyvinylferrocene.

The porous separator serves to prevent short circuiting between the anode and the cathode. The porous separator typically consists of a single-ply or multi-ply sheet of a microporous polymer such as polyethylene, polypropylene, polyamide, polyimide, or a combination thereof. The pore size of the porous separator is sufficiently large to permit transport of ions, but small enough to prevent contact of the anode and cathode either directly or from particle penetration or dendrites which can from on the anode and cathode.

In one embodiment, the electrochemical cell is a lithium ion battery. Suitable anode materials for a lithium ion battery include without limitation lithium metal, lithiated carbon, or a lithium alloy. Suitable cathode materials for a lithium ion battery include, but are not limited to, electroactive transition metal oxides comprising lithium, such as $LiCoO_2$, $LiNiO_2$, $LiMn_2O_4$, or $LiV_3O_8$. Electrolyte compositions suitable for use in lithium ion batteries are described above.

The electrochemical cells disclosed herein may be used as a power source in various electronic articles such as computers, power tools and telecommunication devices; buildings and other residential and commercial structures; and equipment for construction or transportation such as construction machinery, airplanes, trains, buses, trucks, automobiles and other motorized vehicles.

EXAMPLES

The operation and effects of certain embodiments of the inventions hereof may be more fully appreciated from a series of examples (Examples 1~6), as described below. The embodiments on which these examples are based are representative only, and the selection of those embodiments to illustrate the invention does not indicate that materials, components, reactants, designs, conditions or techniques not described in the examples are not suitable for use herein, or that subject matter not described in the examples is excluded from the scope of the appended claims and equivalents thereof. The significance of the examples is better understood by comparing the results obtained therefrom with the results obtained from certain formulations that are designed to serve as controlled experiments (Controls A~C) and provide a basis for such comparison since they do not contain a carbonate compound of this invention.

The meaning of abbreviations used is as follows: "min" means minute(s), "h" means hour(s), "s" means second(s), "mL" means milliliter(s), "•L" means microliter(s), "g" means gram(s), "mg" means milligram(s), "•g" means microgram(s), "mol" means mole(s), "mmol" means millimole(s), "cm" means centimeter(s), "mm" means millimeter(s), "mbar" means millibar(s), "Pa" means pascal(s), "mtorr" means millitorr, "M" means molar concentration, "wt %" means percent by weight, "Hz" means hertz, "mS" means millisiemen(s), "mA" mean milliamp(s), "V" means volt(s), "mV" means millivolt(s), "$^1$H NMR" means proton nuclear magnetic resonance spectroscopy, "$^{19}$F NMR" means fluorine 19 nuclear magnetic resonance spectroscopy.

Reagent Preparation

Preparation of Methyl 2,2,3,3-Tetrafluoropropyl Carbonate (FS-C)

Methyl chloroformate (130 mL, 159 g, 1.68 mol) was added slowly over a period of 3 hours to a solution of 2,2,3,3-tetrafluoropropanol (132 g, 1.00 mol) in pyridine (300 mL, anhydrous) at −10° C. to 0° C. with magnetic stirring. The reaction mixture was stirred at room temperature overnight. Then, the reaction mixture was mixed with 5% HCl (500 mL) and approximately 50 g of ice, and the resulting mixture was extracted three times with 300 mL portions of ether. The combined organic layer was washed three times with 100 mL portions of 5% HCl, followed by two washes with 100 mL portions of 5% sodium carbonate. The organic phase was then dried over anhydrous sodium sulfate. Ether was removed by rotary evaporation. The crude product (approximately 200 g) was distilled, yielding 166 g (87% yield) of pure methyl 2,2,3,3-tetrafluoropropyl carbonate, also referred to herein as "FS-C". NMR analysis data were consistent with the literature values as reported in U.S. Pat. No. 5,659,062.

Preparation of Methyl 2,2,2-Trifluoroethyl Carbonate (FS-D)

In a dry box, methyl chloroformate (219 mL, 268 g, 2.84 mol) was added slowly to a solution containing 2,2,2-trifluoroethanol (233.5 g, 2.335 mol), pyridine (225 g), and dichloromethane (1.2 L, anhydrous) at −10° C. to 30° C. (the dichloromethane was cooled in a freezer before use), with magnetic stirring. The reaction mixture was stirred at room temperature in the dry box overnight. The reaction mixture was then taken out of the dry box, and was washed with 5% HCl (300 mL), followed by 3 washes with 50 mL portions of 5% HCl, one wash with 5% sodium carbonate (100 mL), and 2 washes with 100 mL portions of brine. The organic phase was then dried over anhydrous sodium sulfate. Dichloromethane was removed by rotary evaporation. The residue liquid was distilled with a spinner band column, yielding 185.4 g (46% yield) of pure methyl 2,2,2-trifluoroethyl carbonate, also referred to herein as "FS-D". NMR analysis data were consistent with literature values (U.S. Pat. No. 5,659,062).

Example 1

Synthesis of (2-Oxo-1,3-dioxolan-4-yl)methyl 2,2,2-trifluoroacetate (FS-A)

To a solution containing 25.0 g (0.212 mol) of glycerol 1,2-carbonate (Aldrich, Milwaukee, Wis.) in 50.0 mL of anhydrous dichloromethane, was added 30 mL of trifluoroacetic anhydride (Aldrich). This mixture was stirred in a dry box for 4 hours. Then, volatile materials were removed by roto-evaporation. The remaining liquid (57 g) was purified by vacuum distillation. The fraction collected at 2 mbar (200 Pa) and 142° C. was selected for notably good purity. The yield of 2-oxo-1,3-dioxolan-4-yl)methyl 2,2,2-trifluoroacetate, also referred to herein as FS-A, was 34 g (75%). The final product was analyzed by $^1$H NMR and $^{19}$F NMR as follows:

$^1$H NMR (CDCl$_3$): • 5.04 (m, 1H), 4.66 (dd, 1H, J=3.3, 12.6 Hz), 4.64 (t, 1H, J=8.8 Hz), 4.51 (dd, 1H, J=4.7, 12.5 Hz), 4.34 (dd, 1H, J=6.1, 9.0 Hz). $^{19}$F NMR (CDCl$_3$): • −75.3 (s, CF$_3$).

Example 2

Synthesis of (2-Oxo-1,3-dioxolan-4-yl)methyl 2,2-difluoroacetate (FS-B)

To a solution containing 8.50 g (71.8 mmol) of glycerol 1,2-carbonate (Aldrich, Milwaukee, Wis.) in 30.0 mL of anhydrous dichloromethane, was added 25.0 g (143 mmol) of difluoroacetic anhydride (SynQuest Laboratories, Inc., Alachua, Fla.) at 0-5° C. The resulting mixture was stirred in a dry box for 3 hours. Then, volatile materials were removed by roto-evaporation. The remaining liquid was purified by vacuum distillation. Fractions were collected at 40 mtorr (5.3 Pa), 130-132° C. (4.33 g) and 40 mtorr (5.3 Pa), 138-140° C. (4.50 g). The later fraction was selected as having notably good purity. The yield of 2-oxo-1,3-dioxolan-4-yl)methyl 2,2-difluoroacetate, also referred to herein as FS-B, was 63%. The final product was analyzed by $^1$H NMR and $^{19}$F NMR as follows:

$^1$H NMR (CDCl$_3$): • 6.01 (t, 1H, J=52.9 Hz), 5.03 (m, 1H), 4.63 (t, 1H, J=8.8 Hz), 4.59 (dd, 1H, J=3.3, 12.6 Hz), 4.59 (dd, 1H, J=3.3, 12.6 Hz), 4.45 (dd, 1H, J=4.7, 12.5 Hz). $^{19}$F NMR (CDCl$_3$): • −75.3 (d, 2F, J=52.6 Hz).

Examples 3~6

Controls A~B

Preparation of Nonaqueous Electrolyte Solutions

These formulations describe the preparation of nonaqueous electrolyte solutions containing lithium hexafluorophosphate in two-component solvents. The nonaqueous electrolyte solutions were prepared by weighing predetermined amounts of the components into vials in a dry box. The lithium hexafluorophosphate (LiPF$_6$) (battery grade, Stella Chemifa Corp., Tokyo, Japan) was weighed into each vial to give a final concentration of 0.5 M. Then, the first electrolyte solvent and the second electrolyte solvent were weighed into each vial to give the desired weight percent (wt %) of each component. The compositions of the electrolyte solvents are summarized in Table 1. The electrolyte solvents ethyl methyl carbonate (EMC) and ethylene carbonate (EC) were battery grade, obtained from Ferro Corp. (Cleveland, Ohio).

TABLE 1

Compositions of Nonaqueous Electrolyte Solutions

|  | LiPF$_6$ (M) | First Electrolyte Solvent (wt %) | Second Electrolyte Solvent (wt %) |
| --- | --- | --- | --- |
| Control A | 1.0 | EMC (63%) | EC (37%) |
| Control B | 0.5 | FS-C (70%) | EC (30%) |
| Control C | 0.5 | FS-D (70%) | EC (30%) |
| Example 3 | 0.5 | FS-C (70%) | FS-A[a] (30%) |
| Example 4 | 0.5 | FS-C (70%) | FS-B[b] (30%) |

TABLE 1-continued

Compositions of Nonaqueous Electrolyte Solutions

|  | LiPF$_6$ (M) | First Electrolyte Solvent (wt %) | Second Electrolyte Solvent (wt %) |
| --- | --- | --- | --- |
| Example 5 | 0.5 | FS-D (70%) | FS-A[a] (30%) |
| Example 6 | 0.5 | FS-D (70%) | FS-B[b] (30%) |

[a]Prepared as described in Example 1.
[b]Prepared as described in Example 2.

Electrolyte Ionic Conductivity

The electrical conductivity of the nonaqueous electrolyte solutions described in Examples 3-6 and Controls A~B was measured using ac impedance spectroscopy over the frequency range of 0.1 to 1,000,000 Hz. The impedance results were fit with an equivalent circuit model to yield the dc resistance.

An electrical probe containing two wires was first calibrated over the conductivity range of 10 to 100,000 Hz using standard aqueous solutions of sodium chloride. Then, the electrical probe was placed in the nonaqueous electrolyte solution to be measured. Ionic conductivity measurements were recorded at temperatures of 20-28° C. in a dry box. Results were extrapolated to 25° C. using the temperature dependence of 2.0%/° C. The results summarized in Table 2 are reported at 25° C.

TABLE 2

Ionic Conductivity of Nonaqueous Electrolyte Solutions at 25° C.

| Nonaqueous Electrolyte Solution | Ionic Conductivity (mS/cm) |
| --- | --- |
| Control A | 9.34 |
| Control B | 2.81 |
| Control C | 4.39 |
| Example 3 | 0.50 |
| Example 4 | 0.43 |
| Example 5 | 0.93 |
| Example 6 | 0.81 |

Electrochemical Stability to Oxidation

Measurements of electrochemical stability of certain of the above formulations were carried out in a three terminal electrochemical cell with a salt bridge connecting the sample chamber to a chamber containing a reference electrode.

Measurements were made using 1.6 mm diameter platinum working electrodes with a platinum wire counter electrode, all located in the sample chamber. Approximately, 0.6 mL of a nonaqueous electrolyte solution, as described in Examples 3, 5 and 6 and Controls A~B, was added to the sample chamber for the measurement. The reference electrode was a silver wire in a solution containing 0.01 M LiPF$_6$ in propylene carbonate. The reference electrode chamber was connected to the sample chamber via a salt bridge containing 1.0 M LiPF$_6$ solution in propylene carbonate. A Vycor® porous glass frit (BASi, West Lafayette, Ind.) was used to separate the salt bridge from the sample chamber and the reference electrode chamber.

The electrochemical measurements were made using a PAR 273A potentiostat (AMETEK Princeton Applied Research, Oak Ridge, Tenn.), which was controlled by CorrWare® software (Scribner Associates Inc., Southern Pines, N.C.) using the following procedure. Wires were attached to the electrodes and the open circuit potential was allowed to stabilize. Then, the potentiostat potential applied to the working electrode was set to the open circuit potential. The applied potential was ramped at a rate of 10 mV/s from the open circuit potential to a potential of 4.0 V versus the Ag/Ag$^+$ reference electrode and the current was recorded as a function of potential.

The results were compared at a current density of 1.0 mA/cm$^2$ and are summarized in Table 3.

TABLE 3

Electrochemical Stability of Electrolytes to Oxidation

| Nonaqueous Electrolyte Solution | Potential of Pt Electrode versus Reference Electrode (V) at a Current Density of 1.0 mA/cm$^2$ |
| --- | --- |
| Control A | 2.25 |
| Control B | 2.97 |
| Control C | 2.89 |
| Example 3 | 3.33 |
| Example 5 | 3.11 |
| Example 6 | 3.37 |

The current results from electrochemical oxidation on the cathode and a high cathode potential for a current density of 1.0 mA/cm$^2$ are indicative of an electrolyte composition that is stable at higher potentials. Specifically, the electrolyte compositions containing the fluorinated electrolyte solvents of the invention are oxidized at higher potentials than those containing EC.

Electrolyte Performance in Lithium Ion Batteries

Electrochemical cells (2032 coin cells) were prepared with graphite/copper anodes (Pionics Co., Ltd., Shiga, Japan), LiCoO$_2$/copper cathodes (Pionics Co., Ltd.) and a polyethylene/polypropylene separator (Celgard® battery separator, Celgard LLC., Charlotte, N.C.). The nominal cathode loading was 1.5 mA-h/cm$^2$ based on the initial discharge capacity for cycling with a standard battery electrolyte (Control C) between 2.7 V and 4.2 V at a current of 0.25 mA.

Circular pieces of the separator were cut with a ¾ inch arch punch and the pieces were transferred to a glovebox. Circular sections of cathodes were cut with a 9/16 inch arch punch. The resulting cathodes had a nominal cathode loading of 2.5 mA-h based on conversion of LiCoO$_2$ to Li$_{0.5}$CoO$_2$. Circular sections of the anodes were cut with a ⅝ inch arch punch. The pre-cut cathode and anode sections were heated to 90° C. for 12 hours under vacuum in an antechamber, and then transferred to a glovebox.

The coin cells consisted of coin cell cases (SUS316L), spacer disks, wave springs, and caps, and a polypropylene casket, all obtained from Hohsen Corp. (Osaka, Japan). The coin cell components were sonicated in ultra-high purity water with detergent for one hour, rinsed with ultra-high purity water for 60 min, and then dried at 90° C. under house vacuum. The cleaned coin cell components were transferred to a glovebox.

A circular cathode section was placed in the coin cell case and 4 drops (about 0.2 mL) of the nonaqueous electrolyte solution to be tested, as described in Examples 5 and 6 and Control A, were added. A circular anode section was then placed on the wetted cathode. The circular anode section was placed on top of the separator. The spacer disk was set on the anode and all layers were aligned in the center of the coin cell case. The wave spring was set on top of the spacer disk and aligned. The gasket was attached to the cap and the gasket-cap assembly was set on top of the wave spring. The assembly was placed in a coin cell battery crimper (Hohsen Corp.) and pressure was applied to seal the coin cell.

The coin cell batteries were tested in an Arbin battery tester (Arbin Instruments, College Station, Tex.). The coin cell batteries were charged to 4.2 V at a constant current of 0.25 mA, held at open circuit for 10 min, and then discharged to 2.7 V at a constant current of 0.25 mA. The coin cell batteries were next held at open circuit for 10 min and then charged again to 4.2 V at a constant current of 0.25 mA. This process was repeated for 5 charge-discharge cycles. The discharge capacity was recorded by integrating the current during the discharge part of the cycle. The discharge capacity is provided as a function of the cycle number in Table 4 for the electrolyte compositions of Control A and Examples 5 and 6. These coin cell batteries demonstrate the utility of the compositions of the invention in lithium ion secondary batteries.

TABLE 4

Discharge Capacity versus Cycle Number for Electrolytes

| | Discharge Capacity (mA-h) | | |
| --- | --- | --- | --- |
| Cycle Number | Control A | Example 5 | Example 6 |
| 1 | 2.515 | 1.916 | 2.091 |
| 2 | 2.493 | 1.884 | 1.990 |
| 3 | 2.477 | 1.834 | 1.900 |
| 4 | 2.465 | 1.775 | 1.923 |
| 5 | 2.454 | 1.747 | 1.865 |

In addition to vendors named elsewhere herein, various materials suitable for use in the inventions hereof may be made by processes known in the art, and/or are available commercially from suppliers such as Alfa Aesar (Ward Hill, Mass.), City Chemical (West Haven, Conn.), Fisher Scientific (Fairlawn, N.J.), Sigma-Aldrich (St. Louis, Mo.) or Stanford Materials (Aliso Viejo, Calif.).

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

In this specification, unless explicitly stated otherwise or indicated to the contrary by the context of usage, amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value;

What is claimed is:

1. A compound as represented by the following structure:

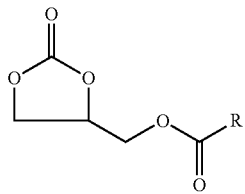

wherein R is a $C_1$ to $C_4$ fluoroalkyl group.

2. A compound according to claim 1 wherein R is $CF_3$.

3. A compound according to claim 1 wherein R is $CF_2H$.

4. A process for preparing a compound according to claim 1 comprising the step of combining, optionally in a solvent, glycerol 1,2-carbonate and $(RfCO)_2O$ or RfCOX, wherein Rf is a $C_1$ to $C_4$ fluoroalkyl and X is a halogen.

5. A process according to claim 4 wherein $(RfCO)_2O$ is $(CF_3CO)_2O$.

6. A process according to claim 4 wherein $(RfCO)_2O$ is $(CF_2HCO)_2O$.

7. A process according to claim 4 wherein the solvent is selected from the group consisting of dichloromethane, chloroform, ether and tetrahydrofuran.

8. A composition comprising a compound according to claim 1 in admixture with at least one electrolyte salt.

9. A composition according to claim 8 further comprising at least one co-solvent selected from the group consisting of ethyl methyl carbonate, dimethyl carbonate, diethyl carbonate, ethylene carbonate, propylene carbonate, vinylethylene carbonate, fluoroethylene carbonate, 2,2,2-trifluoroethyl carbonate, and methyl 2,2,3,3-tetrafluoropropyl carbonate.

10. A composition according to claim 8 wherein the electrolyte salt is selected from the group consisting of lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide, lithium bis(oxalato)borate, $Li_2B_{12}F_{12-x}H_x$ where x is equal to 0 to 8, and mixtures of lithium fluoride and $B(OC_6F_5)_3$.

11. A composition according to claim 10 wherein the electrolyte salt is lithium hexafluorophosphate.

12. A composition according to claim 8 wherein R is $CF_3$.

13. A composition according to claim 8 wherein R is $CF_2H$.

14. An electrochemical cell comprising (a) a housing; (b) an anode and a cathode disposed within the housing; (c) a porous separator disposed within the housing between the anode and the cathode; and (d) an electrolyte composition disposed within the housing in contact with the anode, the cathode and the porous separator and providing an ionically-conductive pathway between the anode and the cathode, wherein the electrolyte composition includes at least one electrolyte salt and a compound according to claim 1.

15. An electrochemical cell according to claim 14 wherein R is $CF_3$.

16. An electrochemical cell according to claim 14 wherein R is $CF_2H$.

17. An electrochemical cell according to claim 14 which is a lithium ion battery.

18. An article comprising an electrochemical cell according to claim 17.

* * * * *